United States Patent [19]

McCoy

[11] 4,226,807

[45] Oct. 7, 1980

[54] PROCESS FOR MAKING ETHER SULFONATES

[75] Inventor: David R. McCoy, Austin, Tex.

[73] Assignee: Texaco Development Corp., White Plains, N.Y.

[21] Appl. No.: 46,271

[22] Filed: Jun. 7, 1979

Related U.S. Application Data

[63] Continuation-in-part of Ser. No. 881,286, Feb. 27, 1978, abandoned.

[51] Int. Cl.² .................. C07C 143/42; C07C 143/02
[52] U.S. Cl. ............................ 260/512 R; 260/513 R
[58] Field of Search ....................... 260/512 R, 513 R

[56] References Cited

U.S. PATENT DOCUMENTS 4,091,014   5/1978   Johnson et al. .................. 260/512 R

*Primary Examiner*—Alan Siegel
*Attorney, Agent, or Firm*—Carl G. Ries; Robert A. Kulason; James L. Bailey

[57] ABSTRACT

Covers a method of sulfonating organic alcohols to prepare ether sulfonates thereof by reacting said organic alcohol compound with a hydroxy-containing alkyl sulfonic salt utilized in solid form under carefully controlled conditions comprising use of a vacuum less than about 300 mm of mercury, while for at least the majority of the reaction period dispersing through the liquid reaction mass an inert gas. The improvement comprising the gist of the invention includes having present at the start of said reaction period a small amount of said product ether sulfonate.

15 Claims, No Drawings

PROCESS FOR MAKING ETHER SULFONATES

REFERENCE TO RELATED APPLICATIONS

This application is a continuation-in-part application of copending application Ser. No. 881,286, filed Feb. 27, 1978 now abandoned.

BACKGROUND OF THE INVENTION

1. Field of the Invention

This invention relates to an improvement of sulfonating organic compounds containing an alcoholic hydroxyl group to produce ether sulfonates useful as detergents and as surfactants for enhanced oil recovery processes.

2. Description of the Prior Art

Organic sulfonic acids and organic sulfonates are becoming increasingly important due to their use in the preparation of liquid detergents, particularly in the preparation of relatively salt-free detergents having good solubility characteristics. Even more recently, compounds of this general type have been found to be useful materials when employed as surfactants for enhanced oil recovery processes. In one general scheme sulfonated materials are prepared by sulfonation processes employing concentrated sulfuric acid or oleum. However, using such strong acids leads to the obvious problems of corrosion and/or salt disposal and separation following neutralization of the final reaction mixture to produce salt by-products. In most instances, products containing substantial amounts of the salt cannot be usefully employed, and such salt must be removed.

To obviate the above problems, another method of preparing organic sulfonates involves reacting an organic alcohol containing at least one hydroxyl group with a hydroxy-containing alkyl sulfonic acid salt. Under appropriate conditions, the two compounds are condensed with formation of by-product water to produce an ether sulfonate. A typical sulfonating (more properly sulfoalkylating) reagent here is sodium isethionate also named as the sodium salt of 2-hydroxyethane sulfonic acid.

In many instances use of hydroxy-containing alkyl sulfonic acids or salts such as 2-hydroxyethane sulfonic acid salt or other sulfonating reagents of this type involves one or more process difficulties. For example, in most instances the organic alcohol to be sulfonated and sulfonating reagent of this type are not mutually soluble one in another. As one example, the hydroxy compounds may be liquids at reaction temperatures but are not solvents for the solid, crystalline sulfonic acid salts. Hence, one is faced with a reaction system consisting of both liquid and solid phases with attendant obvious problems.

In still other instances, reactions of the above type are difficult to control or are even uncontrollable in many instances. Thus, for example, excessive foaming may occur which cannot be practically controlled or eliminated. It is important in controlling foaming to remove water by-product during the course of the reaction as such water is formed. However, resort to such well-known expedients as azeotropic distillation of said by-product water has been found to be unsuccessful or minimally useful.

In yet other processes involving the just described classes of reactants, prior art efforts were unsuccessful in that highly colored products were obtained. Yellow, brown or other colored products when used for detergent use, for example, are unsatisfactory. The discolored product requires bleaching in order to compete with like generally colorless products, which bleaching step adds considerably to the cost of production. In still other instances, sulfonation processes of this type involving the above reactants cannot be or are difficulty temperature controlled. Lastly, in some situations the proposed prior art sulfonating process cannot be adapted to batch, continuous, or semi-continuous processes, which latitude of choice is extremely desirable.

One excellent process for making ether sulfonates from hydroxy-containing sulfonic acid salts is disclosed in copending, commonly assigned Ser. No. 746,463, filed Dec. 1, 1976. This process in brief, comprises reacting said sulfonic salt with an organic alcohol under carefully controlled conditions comprising use of a vacuum measured at less than 300 mm of mercury, for at least the majority of the reaction while dispersing an inert gas through the liquid reaction mass. However, it has been noted that this process when utilizing a solid sulfonic acid salt gave rise to inhomogeneous reaction mixtures giving low product selectivities and low reaction rates. While, of course, aqueous solutions of the salt may be employed as a reactant source, this expedient does involve some drawbacks. Specifically, while working with an aqueous form of sulfonic acid salt reactant there is created the necessity of carefully metering the solution to the reaction mixture at a prescribed rate to avoid reaction difficulties. In addition, there is noted the necessity of long stripping times in order to remove water introduced. This then involves long equipment turn-around times. Additionally, there is thus noted losses of reactant by steam distillation during said stripping step. Lastly, when it is necessary to ship the sulfonic acid salt reactant to the manufacturing site in such aqueous form one must transport inert water along with the active reactant which consequently involves added shipping cost.

It is therefore a principal object of this invention to provide a process for the sulfonation of organic alcohols through reaction with solid hydroxyl-containing alkyl sulfonic acid salts, which process is free from the just-mentioned disadvantages of the prior at processes.

A specific object of the invention is to provide a method of sulfonating organic alcohols via reaction with hydroxyl-terminated lower alkyl sulfonic salts utilized in solid form such as the salt of 2-hydroxyethane sulfonic acid, which reaction can be controlled and produces the desired ether sulfonate products in relatively high yields and high product selectivities concomitant with a desired high reaction rate.

The above-mentioned objects and advantages of the present invention will become apparent as the invention is more thoroughly discussed hereinafter.

SUMMARY OF THE INVENTION

In its broadest aspects the present invention comprises a method of sulfonating an organic compound having at least one alcoholic hydroxyl group which comprises the steps of reacting said alcoholic compound with a hydroxy-containing alkyl sulfonic acid salt utilized in solid form by forming a reaction mass of said alcoholic compound and said sulfonic acid salt and carrying out said sulfonating reaction under a vacuum less than about 300 mm of mercury and for at least the majority of said reaction period while continuously dispersing through said reaction mass an inert gas. The improvement comprising the gist of the invention involves having present at the start of said reaction period a small amount of said product ether sulfonate.

DESCRIPTION OF THE PREFERRED EMBODIMENTS

In more detail, the practice of the present invention relates to a liquid phase method of preparing ether sulfonates of the formula:

R—O—(R$_3$)—SO$_3$A where R is a radical selected from the group consisting of C$_2$–C$_{22}$ alkyl, C$_2$–C$_{22}$ alkenyl, C$_2$–C$_{22}$ hydroxyalkyl, C$_2$–C$_{22}$ hydroxyalkenyl, alkaryl containing one or more C$_1$–C$_{18}$ alkyl groups substituted on said aryl group, aralkyl containing 7–28 carbon atoms, and polyether derivatives of any of the foregoing, R$_3$ is alkylene, and A is an alkali metal cation, which comprises the steps of forming a reaction mass by reacting ROH, where R has the just stated significance with an alkali metal hydroxy-containing alkyl sulfonic acid salt which is utilized in solid form under a vacuum less than about 300 mm of mercury while for at least the majority of said reaction period continuously dispersing an inert gas through said reaction mass. In order to add said sulfonic acid salt to said reaction mass in solid form and avoid the problems stated above, particularly of low product selectivity and low reaction rate due to a inhomogeneous reaction mixture, it is necessary to have present at the start reaction period a small amount of said ether sulfonate.

There are essentially two ways to introduce said product sulfonate at the beginning of the reaction. The first, and by far the most desirable method is to merely add to the aqueous reaction mass a very small amount of product ether sulfonate. It has been found that the ether sulfonate which may be added at this stage achieves the aim of the invention whether it is the same ether sulfonate ultimately produced or another ether sulfonate falling within the broadly defined class of products. However, by addition of an extraneous sulfonate one does, of course, introduce some small amounts of product impurity into the final desired product. Thus, it is desirable to add the same specific ether sulfonate at the initiation of the reaction which one is going to ultimately produce.

Usually the amount of product sulfonate added to the aqueous reaction mass ranges from a very small but effective amount up to about 5 weight percent based on the total weight of reactants utilized. In the more typical case from about 0.1 to about 2.0 weight percent of product is added to the beginning of the reaction.

Alternatively, but not the preferred practice is to heat the alcohol, most preferably, in presence of an alkali metal catalyst such as potassium hydroxide to above the reaction temperature and then add the solid hydroxy-containing alkyl sulfonic acid salt. In such case, even when no vacuum is applied, small quantities of product sulfonate will immediately form and cause the just-discussed desired effect upon the reaction.

In one preferred embodiment of the invention, a process of making ether sulfonates of the formula:

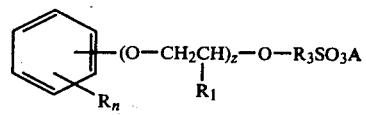

is carried out according to the directions just set out. Here R is a C$_1$–C$_{22}$ alkyl group, n is an integer of 1–3, R$_1$ is hydrogen or methyl, z is an integer of 1–40, R$_3$ is ethylene or propylene and A is an alkali metal cation. In this instance an alcoholic compound of the formula:

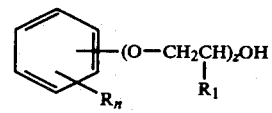

where R, n, R$_1$ and z have a significance as just discussed is reacted with a compound of the formula:

HOR$_3$SO$_3$A where R$_3$ and A are as just mentioned. Again, the reaction is carried out under proper vacuum control while dispersing an appropriate inert gas through the liquid reaction mass.

The process of the present invention is adaptable to sulfonating a wide variety of organic compounds having at least one alcoholic hydroxyl group capable of reacting with an alkali metal hydroxyl-terminated alkyl sulfonic acid salt by way of condensation through respective hydroxyl groups. Such alcohols under the conditions of the process should be relatively non-volatile and therefore available for reaction in liquid form under vacuum. Usually they have a molecular weight greater than 200 and more often greater than 250. Fatty alcohols containing from about 8 to about 20 carbon atoms which may be sulfonated include such as lauryl alcohol, cetyl alcohol, tallow alcohol, octadecyl alcohol, and eicosyl alcohol.

Other non-volatile alcohols which may be sulfonated here include the so-called Oxo alcohols from the Oxo process, vinyldiene alcohols, Ziegler-type primary linear alcohols prepared from trialkylaluminum mixtures made by way of ethylene polymerization, subsequent oxidation, and hydrolysis of the resultant aluminum alkoxides as set out in U.S. Pat. No. 3,598,747 and other alcohols of this type. Typical vinyldiene alcohols are set out in U.S. Pat. No. 3,952,068 and have the general structure

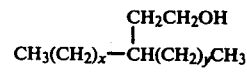

wherein individually, x and y are members from 1 to 15 and the sum of x and y is in the range of 6 to 16.

Polyhydric alcohols may also be employed in the process of the invention including such polyhydric alcohols as aliphatic polyhydric alcohols including the aliphatic glycols, such as, for example, the glycol ethers. Higher functionality polyhydric materials which may be employed include such as glycerol, sorbitol, trimethylolpropane, 1,2,6-hexanetriol, pentaerythritol and the like. Also, suitable are dihydric aromatic materials such as bisphenol-A and hydrogenated bisphenol-A.

Preferred polyhydric alcohols are the aliphatic glycols having 10 or more carbon atoms and the aliphatic glycol ethers having from 10 to 20 carbon atoms.

Phenols and alkyl substituted phenols may also be employed here. Thus, for example, exemplary phenolic reactants include nonylphenol, dinonylphenol, cresol, and the like. Particularly preferred are alkyl substituted phenolic compounds falling within the following structural formula:

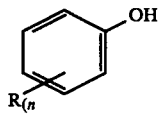

where R is preferably an alkyl group containing from 6 to 20 carbon atoms or a halo, nitro, or hydroxy alkyl substituted group of the same chain length, and n has average values from 1-3. Most typically R in the above formula is a $C_{8-12}$ alkyl group.

Another useful class of reactant alcohols here are those prepared by alkoxylating any of the above class of alcohols or others. Thus, the above compounds may be reacted with ethylene oxide, propylene oxide, butylene oxide or higher alkylene oxides having up to 18 carbon atoms or mixtures thereof. When mixed oxides are used, they may be added to the hydroxy or polyhydroxy compound either sequentially to form block polyether polyol compounds, or may be mixed and reacted simultaneously to form a random, or heteric oxyalkylene chain. The reaction of an alkylene oxide and a hydroxy or polyhydroxy compound is well-known to those skilled in the art, and the base-catalyzed reaction is particularly described in U.S. Pat. Nos. 3,655,590; 3,535,307 and 3,194,773. If diols, triols, tetrols and mixtures thereof are alkoxylated polyether polyols may be obtained which have a molecular weight of from about 500 to about 10,000. These polyether polyols are well-known and may be prepared by any known process such as, for example, the processes described in Encyclopedia of Chemical Technology, Vol. 7, pages 257-262, published by Interscience Publishers, Inc.

A greatly preferred class of hydroxy reactants here include the compounds falling within the following formula:

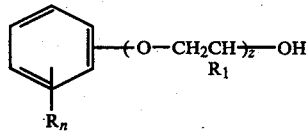

where R is a $C_1-C_{22}$ alkyl group and n is an integer of 1-3, $R_1$, is hydrogen or an alkyl group of 1-18 carbon atoms, and z is a number ranging from 1 to 40. Z more preferably is 1-10 and most preferably is 2-6. Preferably $R_1$ is hydrogen or methyl, z is 1-10, and R is $C_6-C_{20}$, most preferably $C_8-C_{12}$.

Still other alcohols are aralkanols, preferably containing a total of from about 7 to about 28 carbon atoms. These may be represented by the following formula:

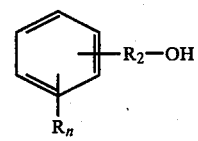

where $R_2$ is an alkylene group containing 1-22 carbon atoms, and R is a $C_1-C_{22}$ alkyl group and n is an integer of 1-3. Polyether derivatives of these compounds may also be made by appropriate alkoxylation.

Thus, preferred alcohols which may be employed as reactants in preparing ether sulfonates are those having the general formula ROH, where R is a radical selected from the group consisting of $C_2-C_{22}$ alkyl, $C_2-C_{22}$ alkenyl, hydroxy or polyhydroxy derivatives of these alkyl or alkenyl compounds, alkaryl radicals containing one or more $C_1-C_{18}$ alkyl groups substituted on said aryl group, and aralkyl radicals containing 7-28 carbon atoms, and polyether derivatives of any of the foregoing.

The sulfonating agent used here is an alkali metal hydroxyalkyl sulfonic acid salt, added to the liquid reaction mass in solid form. Most preferably, the sulfonating agent is an alkali metal hydroxy-terminated straight chain alkyl sulfonic acid salt. Thus, the sulfonating agent employed here has the following structural formula:

$$HOR_3SO_3A$$

where $R_3$ is a straight or branched alkylene group, which optionally may contain other non-interfering groups such as halo, nitro, nitrile, etc. groups. More preferably, $R_3$ is a straight or branched chain unsubstituted alkylene group such as methylene, ethylene, propylene, butylene, pentylene, hexylene and higher alkylene groups. Most preferably, $R_3$ contains 1-4 carbon atoms, and in a greatly preferred embodiment is ethylene or propylene. A represents an alkali metal cation such as sodium, lithium, and potassium.

In a greatly preferred embodiment of the invention, the sulfonating agent, $HOR_3SO_3A$ is one where $R_3$ is ethylene or propylene, most preferably ethylene, and A is an alkali metal cation, most preferably potassium or sodium.

In carrying out the method of preparing the desired ether sulfonates, it is preferred that the vacuum expedient be such that the reaction is effected under a vacuum less than about 100 mm of mercury. In the most preferred embodiment, the process is carried out under a vacuum of 2-100 mm.

A wide variety of inert gases may be chosen as dispersing media, and their choice will be evident to those skilled in the art. Due to the availability and cost, nitrogen is preferred. However, other gases such as argon, helium, xenon, etc. may be employed.

In describing the process of the invention in more detail hereinafter for purpose of convenience, the organic reactant compound containing at least one alcoholic hydroxyl group will be termed "alcohol", and the hydroxy-containing alkyl sulfonic acid salt thereof will be referred to as "sulfonating agent". The product of the reaction will be simply referred to as "ether sulfonate".

With respect to reactant ratios, it has been found that ordinarily it is a preferred expedient to employ at least a slight excess of alcohol versus sulfonating agent. The excess alcohol present usually in liquid form acts as a "heat sink" during reaction, and may later act as a carrier for the product. Usually, from about 1.2 to about 2.5 moles of alcohol is present per mol of sulfonating agent, and more often the mol ratio is 1.5-2:1. However, in the broadest aspects of the invention aspects the molar ratio of alcohol to sulfonating agent can vary from 10:1 or higher to 1:2.

The reaction itself is base-catalyzed. Normally, a strong base is employed such as sodium hydroxide, or potassium hydroxide. Again, the amount of base utilized can vary widely. Usually, however, the ratio of base to alcohol varies from about 0.025:1 to 0.25:1. As a practical matter, the amount of base which one utilizes can be determined by the fact that if the base content is too low, an undesirably slow reaction results. On the other, if excess base is employed while a rapid reaction occurs, undesirable decomposition of the sulfonating agent may also result. One way of utilizing the base catalyst is to add the base along with sulfonating agent to the alcohol. However, it has been found greatly desirable to first form the alkoxide of the alcohol by addition of base thereto prior to addition of the sulfonating agent. The base may be added as a concentrated aqueous solution of say potassium hydroxide or sodium hydroxide in an amount sufficient to give the above mol ratio of base to alcohol. Preferably then the water added along with the base and the water produced by the formation of the alkoxide are removed before solid sulfonating agent is added. This may be done by heating the reaction vessel containing alcohol and base under conditions of vacuum and inert gas purge to remove the water and obtain a clear, dry solution of alkoxide in alcohol. Agitation is normally applied during this step and thereafter.

The minute bubbles of gas have been found to have a dual purpose. They greatly assist in removing water of reaction as well as water added when an aqueous solution of sulfonating agent is employed. More importantly, the gas in some manner tends to moderate the reaction. Without benefit of gas, violent boiling occurs and mechanical carry-out of products and reactants takes place. The presence of gas dispersion tends to greatly dispel these objectional features, and prevent any substantial foaming during processing.

In a typical procedure the alcohol is charged to the reaction vessel along with product ether sulfonate (preferably the same product to be produced in the reaction), along with an aqueous solution of catalyst base such as potassium hydroxide. Agitation is applied and alkoxide compound formed as just noted. Vacuum is applied and inert gas purge is initiated. The nitrogen or other gas purge is introduced into the reaction well below the liquid surface, preferably near the bottom of the kettle so that the gas is dispersed in the liquid as fine bubbles.

After all introduced water is removed by means of vacuum assisted by the inner gas purge, solid sulfonic acid salt reactant is then added and the reaction condensed. Usually, the removal of water prior to addition of sulfonic acid salt reactant is effected at a temperature below the reaction temperature, say 100°-150° C. Thereafter the liquid reaction mass containing added solid sulfonic acid salt reactant is heated to the reaction temperature.

The volume of gas purge or flow rate will depend upon a number of factors including temperature of reaction, reactor vessel size, proportions of reactants, particular reactants employed, etc. Usually the flow rate is most dependent upon the size of the apparatus utilized. As one guide line, the volume of gas purge may be arrived at empirically by using that quantity of purge gas that will increase the pressure of the system (under vacuum) from full vacuum pressure with no purge to 30-60 mm mercury pressure with purge. In a typical case in a 1 liter laboratory kettle, the nitrogen flow rate is about 2 liters/min.

It has been found that both the combination of high vacuum and purge with inert gas are necessary to achieve a high product conversion. Without inert gas, for example, the above described condition of improper process control will occur. On the other hand, without utilization of the vacuum expedient low product conversion figures are obtained.

By utilizing vacuum and inert gas purge as described herein, one can realize product yields in terms of conversion of sulfonating agent greater than about 45%, and more often greater than 50%. In the usual case 55-75% of the sulfonating agent is converted to product. Most often that percentage is 60-70%, and in the optimum situation yields may be 70-80%.

After addition of solid sulfonating agent to alcohol has been completed in the manner generally outlined above, the actual reaction period or digestion period takes place with application of heat. The temperature of reaction should be as high as possible to effect a rapid complete reaction but should be less than the decomposition temperature of the sulfonating agent added in salt form. The temperature of reaction thus should be less than the melting point of the salt. For example, with respect to sodium isethionate the maximum temperature should be less than the melting point or approximately 190° C. In the usual case, then the temperature of reaction should be from slightly less than the melting point of salt to about 10°-2° C. lower than that temperature. Again, with respect to sodium isethionate, the temperature of reaction should then be approximately 180°-190° C. Depending upon the sulfonating agent used, and other process variables the temperature of reaction will usually fall between about 120° C. and 250° C. and more often is 150°-250° C., most often 180°-250° C.

The digestion period or period of reactivity is carried out until the concentration of active ingredient (A.I.) has reached a maximum, at which time the reaction is quenched. It has been found that the concentration of active ingredient after reaching a maximum begins unexpectedly to materially decline. Thus, it is important to terminate the reaction after maximum conversion is reached. It is thought, that some type of decomposition occurs here or that the active product reacts further to a non-active product.

In order to terminate the reaction when the A.I. has reached a maximum, the preferred procedure is to monitor the course of the reaction during the digestion period by titrating samples periodically for A.I. content. In this manner, the reaction can be stopped when the A.I. content is at or near its maximum value. One method of analysis to determine A.I., particularly applicable to those sulfonates with a chain length of $C_8$ or greater, involves a 2-phase titration with mixed indicators. Essentially a solution of anionic surfactant is titrated with a standard solution of a quaternary ammonium cationic salt in the presence of mixed indicators (dimidium bromide and disulfine blue) in a 2-phase (aqueous:chloroform) titration system.

In more detail this titration procedure is run as follows:

1. Weigh approx 1 g sample into a 150-ml breaker by smearing it on the sides of the beaker. Drop in a magnetic stirring bar.
2. Pipet in 100 ml of 10% (V/V) ethyl alcohol in water.
3. Dissolve the sample with stirring.
4. Transfer an aliquot (2 to 5 ml) to the titration bottle.
5. Add water from a graduated cylinder to bring the sample aliquot to 5 ml.
6. Add:
a. 10 ml 10% $Na_2SO_4$ solution.
b. 5 ml of acid indicator sol.
15 ml of chloroform.
7. Titrate with standard Hyamine 1622 until bottom phase turns from pink to blue and all traces of purple are gone.
8. Calculate A.I. in meq/g or % as follows:

$$\text{A.I., meq/g} = \frac{\text{ml Hyamine} \times \text{N Hyamine} \times 100}{\text{ml Sample Aliquot} \times \text{Sample Wt.}}$$
$$\text{A.I., \%} = (\text{A.I., meq/g}) \times (\text{meq. wt. surfactant}) \times (100)$$

The amount of time to reach maximum conversion will vary widely depending upon the reactants employed, temperature of reaction, reaction mass size, etc. As a guideline it usually takes 178 -1 hour to complete a small laboratory preparation say 1 liter. Scaling up to a five gallon batch usually involves a reaction time of 2-4 hours, while carrying out reaction in a 2,000 gallon reactor takes approximately 6-7 hours. Time of reaction then may vary from about ¼ hour to about 24 hours.

After maximum conversion is reached by measurement of A.I. content, the reaction mass is cooled. By cooling, decrease in A.I. content is reduced or substantially prevented and, in addition, any loss in A.I. content caused by hydrolysis of product when subsequently diluted with water is kept to a minimum. If a hot reaction mass is diluted to prepare product in a final diluted form suitable for use, A.I. losses can run as high as 10-20% upon dilution. It has also been found that one may slow the rate of decrease in A.I. content by breaking the vacuum (but retaining the inert gas purge) after maximum conversion has been obtained.

After completion of the reaction as noted above, usually the reaction mass is diluted. In most instances, the dilution water is first acidified to give an essentially neutral diluted final product.

As a last step in the process, and in a preferred embodiment, product extraction is carried out. It has been found that in order to separate the ether sulfonate product from unreacted or excess alcohol an extractant such as a water-organic ester such as ethyl acetate system or an organic ketone-hydrocarbon-water extractant solvent system may be most usefully employed. The last mentioned solvent system preferably is a mixture of benzene, acetone and water. In first attempted purifications of product, it was originally found that fractionation by use of immiscible organic solvents was not satisfactory. On the other hand, when water was used many solvents also employed were emulsified by the sulfonated surfactant products. However, by use of the just mentioned mixtures, good separation was achieved, as will be shown hereinafter in more specific detail.

With respect to use of an inert gas purge, it is interesting to note that merely blanketing the reaction with an inert gas or putting a pad of inert gas such as nitrogen over the liquid reaction mass had no affect in properly controlling the reaction, as compared to the dispersion method described in great detail above. Along this line it should also be noted that resort to some type of azeotropic distillation by removing water of reaction and extraneous water added was not an appropriate technique to properly carry out the process of this invention. Only by resort to vacuum-inert gas feed control can one achieve proper maximum conversion in terms of A.I. and conversion of starting sulfonating agent.

The following examples specifically illustrate the process of the invention. It should be understood, of course, that these examples are merely illustrative and that the invention is not to be limited thereto.

EXAMPLE I

Here a typical run involving use of an aqueous form of sulfonic acid salt was carried out as follows. A flask was charged with 600 parts by weight of

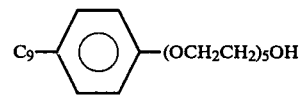

and 5.2 parts KOH dissolved in 5 parts $H_2O$. The mixture was heated with mechanical stirring in a stream of nitrogen at 35 mm Hg pressure to remove $H_2O$. A 57 wt. % aqueous solution of $HOCH_2CH_2SO_3Na$ (143 parts active total) was added to the stirred reaction mixture at 180° C./35 mm Hg pressure over a 125 minute period, while maintaining a $N_2$ sweep rate of approximately 2 cc nitrogen/minute/gram of reaction mixture. The resulting silky, opaque dispersion resulting was digested under the above reaction conditions while periodically sampling the mixture to determine, by 2-phase antagonistic titration with a cationic surfactant, the weight percent active sulfonate product (% AI) in the mixture. The reaction was shut down once the % AI began to drop due to product decomposition. A peak AI of 53.5% was obtained after 90 minutes. Numerous other similar runs carried out on a 56% $HOCH_2CH_2SO_3Na$ solution gave peak AI values of 50-55% at reaction times of 75-95 minutes.

EXAMPLE II

This example was run as outlined in Example I above with the exception that after water was removed from the alcohol-potassium hydroxide at 120° C., the sulfonic acid salt was added to this mixture at once in the form of a crystal and powder. Upon heating at 180° C. the sulfonic acid salt began to form large chunks that only partially dispersed as the reaction proceeded. The peak AI obtained was 36% after 13 minutes digestion.

EXAMPLE III

This example illustrates the process of the invention involving the improvement realized by initial addition of small amounts of product sulfonate.

Specifically, this reaction was carried out as in Example II with the exception that when the alcohol and potassium hydroxide was introduced, in addition 27 parts of crude reaction product from a previous run (20 wt. % active product) was also added. After water was removed at 120° C., solid sulfonic acid salt was added. At the 180° C. reaction temperature a fine grain dispersion resulted. A peak AI of 50 wt. % was obtained after 75 minutes.

EXAMPLE IV

Here the reaction of Example II was carried out with the exception that an aliphatic alcohol ethoxylate was employed.

Specifically, the reaction flask was charged with 220 parts of the alcohol

RO—(CH$_2$CH$_2$O)$_4$H where R represents a C$_{16}$-C$_{18}$-C$_{20}$ straight chain alkyl groups blend, and 1.9 parts of potassium hydroxide and two parts of water. The mixture was heated 120° C. under vacuum to remove the water and then 54.4 parts of solid sodium isothionate was introduced. Digestion at 180° C. only resulted in a gummy percipitate that coated the reactor walls. The reaction was shut down after four hours digestion giving a measured AI of only 1.7 wt. %.

EXAMPLE V

This example was run exactly as Example IV with the exception that the initial charge included 27 parts of crude of reaction mixture from a previous run containing 10 wt. % active ether sulfonate product. A good dispersion of sodium isethionate was obtained at the 180° C. digestion temperature and a peak AI of 48% was reached after 140 minutes.

While, as outlined in Ser. No. 746,563, dry sulfonic acid salt may be utilized in the invention as noted there such expedient can only be effected when the dry reactant is fed at a carefully metered rate. In the present invention, one may add in a desirable manner all of the solid sulfonic acid salt reactant at once without resort to the necessity for controlled feeding of such reactant.

The term "sulfonation", as used here is employed to describe in a short-hand manner the actual and properly termed sulfoalkoxylation reaction such as the sulfoethylation reaction involving reaction of sodium isethionate with an alcohol.

The invention is claimed as follows.

We claim:

1. In a method of preparing ether sulfonates of the formula:

R—O—(R$_3$)—SO$_3$A where R is a radical selected from the group consisting of C$_2$-C$_{22}$ alkyl, C$_2$-C$_{22}$ alkenyl, C$_2$-C$_{22}$ hydroxyalkyl, C$_2$-C$_{22}$ hydroxyalkenyl, alkaryl containing one or more C$_1$-C$_{18}$ alkyl groups substituted on said aryl group, aralkyl containing 7-28 carbon atoms, and polyether derivatives of any of the foregoing, R$_3$ is alkylene, and A is an alkali metal cation which comprises the step of reacting in liquid phase an alcohol, ROH where R has the just stated significance with an alkali metal hydroxy-containing alkyl sulfonic acid salt which is substantially all added in solid form to said alcohol prior to initiation of reaction and so reacted under a vacuum less than about 300 mm of mercury, while for at least the majority of said reaction period continuously dispersing an inert gas through said liquid reaction mass; the improvement which comprises adding a small amount of said ether sulfonate to the reaction mass prior to the initiation of said reaction.

2. The method of claim 1 wherein said sulfonic acid salt reactant is the sodium salt of 2-hydroxyethane sulfonic acid.

3. The method of claim 1 wherein said amount of ether sulfonate added is 0.1-2.0 weight % based on the weight of the reactants.

4. The method of claim 1 wherein said small amount of said ether sulfonate added corresponds chemically to the ether sulfonate produced.

5. The method of claim 1 wherein said reaction is carried out at a temperature less than the melting point of said sulfonic acid salt.

6. The method of claim 5 wherein said temperature of reaction is greater than 180° C.

7. The method of claim 1 wherein said reaction is base-catalyzed.

8. The method of claim 1 where R$_3$ is ethylene or propylene.

9. In a method of preparing ether sulfonates of the formula:

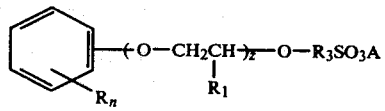

where R is a C$_1$-C$_{22}$ alkyl group, n is an integer of 1-3, R$_1$ is H or CH$_3$, z is an integer of 1-40, R$_3$ is ethylene or propylene and A is an alkali metal anion, which comprises the step of reacting in liquid phase an alcohol compound having the formula:

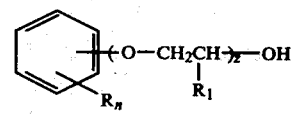

where R, R$_1$, n and z have a significance as above stated with a hydroxy-containing alkali metal alkyl sulfonic acid salt having the formula:

HOR$_3$SO$_3$A where R$_3$ and A have a significance as above stated, which salt is substantially all added in solid form to said alcohol prior to initiation of reaction and so reacted under a vacuum less than about 300 mm of mercury, while for at least the majority of said reaction period continuously dispersing an inert gas through said liquid reaction mass; the improvement which comprises adding a small amount of said ether sulfonate to the reaction mass prior to initiation of said reaction.

10. The method of claim 9 wherein said sulfonic acid salt is the sodium salt of 2-hydroxyethane sulfonic acid.

11. The method of claim 9 wherein said amount of ether sulfonate added is 0.1-2.0 weight % based on the weight of the reactants.

12. The method of claim 9 wherein said small amount of said ether sulfonate added corresponds chemically to the ether sulfonate produced.

13. The method of claim 9 wherein said reaction is carried out at a temperature less than the melting point of said sulfonic acid salt.

14. The method of claim 9 wherein said temperature of reaction is greater than about 180° C.

15. The method of claim 9 wherein said reaction is base-catalyzed.

* * * * *